United States Patent
Leroux et al.

(10) Patent No.: US 11,007,282 B2
(45) Date of Patent: May 18, 2021

(54) COMPOSITIONS FOR CIRCULATORY SYSTEM VISUALIZATION

(71) Applicant: DICRONIS SAGL, Monteggio (CH)

(72) Inventors: Jean-Christophe Leroux, Zürich (CH); Michael Detmar, Boppelsen (CH); Davide Brambilla, Zürich (CH); Steven Proulx, Zürich (CH)

(73) Assignee: DICRONIS SAGL, Monteggio (CH)

( * ) Notice: Subject to any disclaimer, the term of this patent is extended or adjusted under 35 U.S.C. 154(b) by 0 days.

(21) Appl. No.: 15/572,710

(22) PCT Filed: May 10, 2016

(86) PCT No.: PCT/EP2016/060467
§ 371 (c)(1),
(2) Date: Nov. 8, 2017

(87) PCT Pub. No.: WO2016/180835
PCT Pub. Date: Nov. 17, 2016

(65) Prior Publication Data
US 2018/0110882 A1   Apr. 26, 2018

(30) Foreign Application Priority Data
May 11, 2015 (EP) .................................. 15167160

(51) Int. Cl.
*A61K 49/00* (2006.01)
*A61K 9/00* (2006.01)
*A61K 47/32* (2006.01)
*A61K 9/16* (2006.01)

(52) U.S. Cl.
CPC ........ *A61K 49/0034* (2013.01); *A61K 9/0021* (2013.01); *A61K 9/1635* (2013.01); *A61K 47/32* (2013.01); *A61K 49/0069* (2013.01); *A61K 49/0073* (2013.01)

(58) Field of Classification Search
CPC .......................... A61K 49/0034; A61K 9/0021
See application file for complete search history.

(56) References Cited

U.S. PATENT DOCUMENTS

| | | |
|---|---|---|
| 3,964,482 A | 6/1976 | Gerstel et al. |
| 6,334,856 B1 | 1/2002 | Allen et al. |
| 6,503,231 B1 | 1/2003 | Prausnitz et al. |
| 6,611,707 B1 | 8/2003 | Prausnitz et al. |
| 8,708,966 B2 | 4/2014 | Allen et al. |
| 2003/0060718 A1 | 3/2003 | Alam et al. |
| 2012/0004626 A1 | 1/2012 | Kuwahara et al. |
| 2012/0184495 A1 | 7/2012 | Koyakutty et al. |
| 2012/0265145 A1* | 10/2012 | Mefti ............... A61M 37/0015 604/173 |
| 2013/0045167 A1 | 2/2013 | Melles |
| 2015/0018755 A1* | 1/2015 | Chen .................... A61K 9/0021 604/46 |

FOREIGN PATENT DOCUMENTS

| | | |
|---|---|---|
| EP | 1655040 A1 | 5/2006 |
| EP | 2338557 A1 | 6/2011 |
| EP | 2774625 A1 | 9/2014 |
| JP | 2012-025723 A1 | 2/2012 |
| JP | 2012-047684 A1 | 3/2012 |
| WO | WO 2008/005514 A2 | 1/2008 |

OTHER PUBLICATIONS

International Search Report for PCT/EP2016/060467, dated Jul. 18, 2016.
Brambilla et al., "Microneedles for the Noninvasive Structural and Function Assessment of Dermal Lymphatic Vessels," Small 12(8):1053-1061 (2016).
Lee et al., "Fabrication of a novel partially dissolving polymer microneedle patch for transdermal drug delivery," Journal of Materials Chemistry B 3:276-285 (2015).
Chu et al., "Fabrication of Dissolving Polymer Microneedles for Controlled Drug Encapsulation and Delivery: Bubble and Pedestal Microneedle Designs," *J. Pharma. Sci.* 99(10):4228-4238 (2010).
Devoisselle et al., "Fluorescence properties of indocyanine green: II. In-vitro study related to in-vivo behavior," *Proc. SPIE* 2980:293-302 (1997).
Isakau et al., "Toward understanding the high PDT efficacy of chlorin e6-polyvinylpyrrolidone formulations: Photophysical and molecular aspects of photosensitizer-polymer interaction in vitro," *J. Photochem. Photobiol. B* 92(3):165-174 (2008).
Klein et al., "A Randomized Controlled Trial to Optimize Indocyanine Green-Augmented Diode Laser Therapy of Capillary Malformations," *Lasers Surg. Med.* 45(4):216-224 (2013).
Lahiji et al., "A patchless dissolving microneedle delivery system enabling rapid and efficient transdermal drug delivery," *Sci. Rep.* 5:7914 (2015).
Malicka et al., "Metal-enhanced emission from indocyanine green: a new approach to in vivo imaging," *J. Biomed. Opt.* 8(3):472-478 (2003).
Moody et al., "Non-covalent labeling of human serum albumin with indocyanine green: a study by capillary electrophoresis with diode laser-induced q fluorescence detection," *J. Chromatogr. B* 729:55-64 (1999).
Nelson et al., "Minimally invasive method for determining the effective lymphatic pumping pressure in rats using near-infrared imaging," *Am. J. Physiol. Regul. Integr. Comp. Physiol.* 306:R281-R290 (2014).
Ohnishi et al., "Organic Alternatives to Quantum Dots for Intraoperative Near-Infrared Fluorescent Sentinel Lymph Node Mapping," *Mol. Imaging* 4:172-181 (2005).

(Continued)

*Primary Examiner* — James W Rogers
(74) *Attorney, Agent, or Firm* — Medler Ferro Woodhouse & Mills PLLC (57) ABSTRACT

This invention describes compositions comprising indocyanine green and poly(N-vinylpyrrolidone) and methods of making the same as well as applications thereof for diagnostic and therapeutic uses. One of those applications is the structural and functional assessment of the lymphatic system by fluorescence imaging.

7 Claims, 7 Drawing Sheets

(56) References Cited

OTHER PUBLICATIONS

Park et al., "Biodegradable polymer microneedles: Fabrication, mechanics and transdermal drug delivery," *J. Control. Release* 104:51-66 (2005).
Proulx et al., "Quantitative Imaging of Lymphatic Function with Liposomal Indocyanine Green," *Cancer Res.* 70(18):7053-7062 (2010).
Machine translation of JP 2012-025723, published Feb. 9, 2012.
Machine translation of JP 2012-047684, published Mar. 8, 2012.

* cited by examiner

COMPOSITIONS FOR CIRCULATORY SYSTEM VISUALIZATION

This invention describes compositions comprising indocyanine green and poly(N-vinylpyrrolidone) and methods of making the same as well as applications thereof for diagnostic and therapeutic uses. One of those applications is the structural and functional assessment of the lymphatic system by fluorescence imaging.

RELATED ART

The circulatory system is a central player in vertebrate's life. It is in charge of transporting the blood containing several components including nutrients, cells and oxygen throughout the body to nourish it, stabilize its temperature and pH, and to maintain the homeostasis. As many diseases have impact on the circulatory system, its structural and functional monitoring is a fundamental step in several diagnostic procedures. In particular, the monitoring of the vascular function and perfusion of tissues and organs of interest play hereby an important role.

The lymphatic system consists of a network of vessels and nodes which play an essential role in tissue homeostasis by draining lymph from the interstitial space back to the bloodstream. When lymphatic function is impaired, several pathologies may develop, most notably lymphedema, which is characterized by fluid accumulation in the involved limb that may markedly impair the quality of life. In particular, lymphedema is often observed after surgery of breast cancers, and impaired wound healing may be associated with impaired lymphatic function. Lately, it has become clear that disparate pathological conditions (inflammation, cancer growth and metastasis, etc.) strongly correlate with alterations of the lymphatic system. Thus, in several diseases, the assessment of lymphatic vessel structure and function can be exploited for therapeutic and diagnostic purposes.

For instance, the visualization of the lymphatic system can be a clinically relevant tool for mapping the sentinel lymph nodes to characterize early skin cancer staging and for the assessment of lymphatic vasculature architecture and function in lymphatic-vascular disorders. Numerous techniques, including computer tomography, ultrasound, lymphoscintigraphy, magnetic resonance imaging and positron emission tomography, have been used to visualize the lymphatic architecture and functionality. However, due to their prohibitive costs, the lack of appropriate spatial resolution and/or the difficulties to locate and cannulate lymphatic vessels for contrast agent administration, they are not routinely employed. Recently, near-infrared (NIR) imaging has emerged due to its high sensitivity enabling non-invasive assessment of lymphatic architecture and function. At a wavelength range (>750 nm) where photons are minimally scattered or absorbed by biological tissues, NIR imaging and tomography demonstrate excellent spatial resolution for superficial vessels (Nelson, T S et al, Am J Physiol Regul Integr Comp Physiol 306: R281-R290, 2014). Although several organic and inorganic NIR dyes have been proposed, indocyanine green (ICG) remains the only one FDA-approved.

Indocyanine green (ICG) is a negatively charged, water-soluble, dark green tricarbocyanine dye that has been clinically used for over 50 years for the evaluation of hepatic clearance, cardiovascular function and retinal angiography. In particular, the FDA has approved ICG as an injectable contrast agent for use in determining hepatic function, cardiac output and liver blood flow as well as for ophthalmic angiography. In ophthalmic angiography, for example, ICG is excited to fluorescence by radiation, permitting angiograms of the ophthalmic vasculature to be obtained. Furthermore, ICG has a long history of use as a test of cardiac output and liver function as it is excreted exclusively in the bile and has a serum half-life of 3 to 4 minutes after intravenous administration. Moreover, ICG use allows non-invasive monitoring of liver or splanchnic perfusion (by monitoring the changes in the ICG plasma disappearance rate, this method is suitable as a parameter for predicting the probability of survival of intensive-care surgical patients).

In the clinic, the dye is usually reconstituted in injectable water at a concentration in the mg/ml range directly before intravenous administration. Due to its optical properties and protein binding characteristics, ICG imaging has recently been employed for lymphatic drainage quantification/kinetics, sentinel lymph node mapping, and assessment of lymphatic vasculature structure and monitoring of vascular repair after grafting as well as oncology imaging. However, although soluble in water, ICG shows a dramatic fluorescence self-quenching. As a consequence, the fluorescent signal can be low and a phase of fluorescence de-quenching is generally observed within the first hours after in vivo administration, leading to imaging artifacts and difficulties in precise clearance kinetics quantification.

Among the different formulations proposed to bypass ICG-water limitations, the pre-absorption of ICG to serum albumin has gained particular attention. Indeed, the fluorescent signal of ICG is increased in presence of albumin with an optimal molar ratio defined being around 1 and several publications reported improved lymphatic imaging using this formulation (Moody et al. Journal of Chromatography B, 729 (1999), 55-64; Ohnishi et al. Molecular Imaging, 4 (3), 172-181, 2005). Malicka et al discovered that the presence/vicinity of metallic particles (silver) was able to amplify even further the fluorescence intensity of ICG-albumin complex via an increase of radiative decay (Malicka J. et al. Journal of Biomedical Optics, 2003, 8(3) 472-8). However, although simple, the human serum albumin-based formulations bear a number of drawbacks. These include potentially high cost production, non-optimal mechanical properties, in particular when used to prepare microneedle devices, as well as possible immunogenicity after injection especially after sterilization by gamma irradiation or autoclave. Concomitantly, several other strategies have been proposed. Devoiselle et al. observed an increase of fluorescence of ICG in presence of high concentrations of phospholipid and surfactants (Devoiselle et al., SPIE, 1997, 2980, 453-460). U.S. Pat. No. 6,944,493 described an aqueous ICG composition further comprising an alcohol and a stabilizer such as a non-ionic surfactant in order to improve the stability of the ICG solution after reconstitution and to enhance the ICG concentration. EP 2'774'625 described the encapsulation of a fluorescent probe such as ICG within micelles formed by styrene-maleic acid (SMA) copolymers for tumor detection and photodynamic treatment. EP 1'655'040 described the design of an ultrasound contrast agent made of gas filled microbubbles in combination with a visible dye (such as ICG) as an advantageous tool for sentinel lymph nodes visualization before and during surgical excision. Proulx et al. described a PEGylated liposomal formulation of ICG with improved stability in solution and an increased fluorescence signal. When injected intradermally, liposomes were specifically taken up by lymphatic vessels and allowed improved visualization of deep lymph nodes (Proulx et al. Cancer Research. 2010; 70(18):7053-62).

Despite the developments made, rapid and reliable diagnosis still represents a crucial challenge for modern medicine to promptly apply the necessary treatments and to avoid the worsening to more serious disease stages. In particular, there is a critical need for quantitative imaging methods to measure lymphatic flow.

SUMMARY OF THE INVENTION

We have surprisingly found that the combination of poly(N-vinylpyrrolidone) (PVP), a water-soluble polymer made from the N-vinylpyrrolidone monomer, with indocyanine green (ICG) leads to a significant increase in the fluorescence signal of ICG. Surprisingly, this is not only the case for the inventive aqueous composition but for the solid composition of the present invention as well. Thus, it has been surprisingly found that microneedle devices prepared with the inventive compositions of the present invention show an intense fluorescence. This is in particular noteworthy since ICG is typically dissolved in water prior to its use. Moreover, and in particular important for diagnostic applications of the present inventive compositions, the fluorescent signal after administration of the inventive ICG-PVP compositions does not show a fluorescence de-quenching phase, i.e. an increase of fluorescence signal over early time-points as it is the case for ICG-water compositions. This, in turn, allows precise spatial and temporal lymphatics clearance kinetics quantification since the clearance kinetics correlates with lymphatic functionality. The inventive compositions are therefore particularly useful for the real-time quantitative imaging of the vascular system and in particular the lymphatic system. The fluorescent signal at the site of injection can be, preferably, quantitatively visualized using a NIR camera. The non-invasive and rapid evaluation of the lymphatic system using the inventive compositions for the diagnosis of several pathologies such as skin diseases or cancers does represent a crucial step for the appropriate therapy design. Moreover, aside from the ability to increase the ICG fluorescence signal and avoid the fluorescence de-quenching phase, interesting features of using PVP as excipient for the inventive compositions, and in particular for the NIR fluorescence lymphatic system imaging, include its recognized safety, availability in injectable grade and ability to be sterilized by various means including filtration, autoclave and gamma irradiation. Moreover, PVP has already been used as excipient in FDA-approved drugs. Furthermore, and as indicated, ICG is the only NIR dye approved so far by the FDA. Thus, the inventive compositions are, in addition, very beneficial when taking regulatory aspects into account. Moreover, compared to all other previously described ICG formulations and compositions, respectively, the ICG/PVP compositions of the present invention are technically extremely simple, including only few preparation steps in complete absence of harmful materials such as organic solvents or other potentially toxic molecules.

Thus, in a first aspect, the present invention provides for a solid composition comprising (a) indocyanine green (ICG), and (b) poly(N-vinylpyrrolidone) (PVP), wherein the mass ratio of said ICG to said PVP is from 1:150'000 to 1:12.5, wherein preferably the mass ratio of said ICG to said PVP is from 1:100'000 to 1:12.5, wherein further preferably the mass ratio of said ICG to said PVP is from 1:100'000 to 1:37.5, wherein further preferably said mass ratio of said ICG to said PVP is from 1:100'000 to 1:75, wherein again further preferably said mass ratio of said ICG to said PVP is from 1:50'000 to 1:75, and wherein again further preferably said mass ratio of said ICG to said PVP is from 1:20'000 to 1:375. In a preferred embodiment, the PVP has a weight average molecular weight of below 50'000 Dalton, preferably of below 20'000 Dalton, further preferably from 500 to 20'000, again preferably from 500 to 12'000, and again further preferably from 2'000 to 11'000.

In second aspect, the present invention provides for an aqueous composition obtained by dissolving the inventive solid composition in water, preferably in sterilized water, further preferably in water for injection (WFI). Preferably, the concentration of said ICG in said aqueous composition is from 0.025 mg/mL to 20 mg/mL, preferably from 0.025 mg/mL to 9.8 mg/mL, and wherein further preferably the concentration of said ICG in said aqueous composition is from 0.025 mg/mL to 5 mg/mL, again further preferably from 0.1 mg/mL to 5 mg/mL, and wherein the concentration of said PVP in said aqueous composition is from equal to or higher than 0.5 mg/mL, preferably from 0.5 mg/mL to 1.5 g/mL, and wherein further preferably the concentration of said PVP in said aqueous composition is from 7.5 mg/mL to 1.5 g/mL, and again further preferably from 7.5 mg/mL to 0.5 g/mL. In another preferred embodiment, the concentration of said ICG in said aqueous composition is from 0.05 mg/mL to 20 mg/mL, preferably from 0.1 mg/mL to 20 mg/mL, further preferably from 0.1 mg/mL to 5 mg/mL, and wherein the concentration of said PVP in said aqueous composition is from 75 mg/mL to 1.5 g/mL. In another preferred embodiment, the concentration of said ICG in said aqueous composition is from 0.1 mg/mL to 9.8 mg/mL, preferably from 0.1 mg/mL to 5 mg/mL, and wherein the concentration of said PVP in said aqueous composition is from 75 mg/mL to 1.5 g/mL, preferably from 75 mg/mL to 0.5 g/mL.

In a further aspect, the present invention provides for a method of producing the inventive aqueous composition, wherein said method comprises dissolving the inventive solid composition in water, preferably in sterilized water, further preferably in water for injection (WFI).

In another aspect, the present invention provides for a multi-chambered vessel comprising a first container and a second container, wherein said first container comprises the inventive solid composition, and wherein said second container comprises a physiological acceptable aqueous solution or sterile water, preferably water for injection (WFI). Preferably, said multi-chambered vessel is a dual-chamber syringe. Alternatively preferably, the multi-chambered vessel is a vial.

In another preferred aspect, the present invention provides for the use of the inventive solid composition or the inventive aqueous composition in a method of making a microneedle device.

In another aspect, the present invention provides for a microneedle device, preferably comprising a substrate to which a plurality of microneedles are attached or integrally formed, wherein said microneedle device is prepared with the inventive solid composition.

In another aspect, the present invention provides for a microneedle device, preferably comprising a substrate to which a plurality of microneedles are attached or integrally formed, wherein said microneedle device comprises, preferably consists of, the inventive solid composition.

Further aspects of the present invention include the use of the inventive solid composition or the inventive aqueous composition in a method of imaging the circulatory system, preferably of imaging the lymphatic system, further preferably in a method of real-time quantitative imaging the lymphatic system.

In another aspect, the present invention provides for the use of the inventive solid composition or the inventive aqueous composition in a method of obtaining an angiographic image of a tissue or in a method of imaging the perfusion of a tissue, preferably in a method of obtaining an angiographic image of a tissue. Preferably, the tissue is the eye, lung, gastrointestinal tract, bladder, pancreas, gall bladder, sinus, trachea, liver, kidney, heart, cervix, brain, ovary, prostate, stomach or skin, and wherein further preferably said tissue is the eye, heart, liver and stomach.

In another aspect, the present invention provides for the use of the inventive solid composition or the inventive aqueous composition in a method of monitoring the vascular system, preferably of monitoring the lymphatic system, further preferably in a method of real-time quantitative monitoring the lymphatic system, and wherein preferably said monitoring comprises the assessment of the functionality of said vascular system or said lymphatic system.

In another aspect, the present invention provides for a solid composition or an aqueous composition for use in a method of obtaining an angiographic image of a tissue or in a method of imaging the perfusion of a tissue, wherein preferably said tissue is the eye, lung, gastrointestinal tract, bladder, pancreas, gall bladder, sinus, trachea, liver, kidney, heart, cervix, brain, ovary, prostate, stomach or skin, and wherein preferably said tissue is the eye, heart, liver and stomach.

In another aspect, the present invention provides for a solid composition, an aqueous composition or a microneedle device, for use in a method of monitoring the vascular system, preferably of monitoring the lymphatic system, further preferably in a method of real-time quantitative monitoring the lymphatic system, and wherein preferably said monitoring comprises the assessment of the functionality of said vascular system or said lymphatic system.

Moreover, further aspects of the present invention include the inventive compositions for use in therapy of a mammal, preferably of a human. Preferably, said therapy is a photodynamic therapy (PDT), preferably a PDT for skin tumors.

Further aspects of the present invention become evident as this description proceeds.

BRIEF DESCRIPTION OF FIGURES

FIG. 11. Fluorescent signal quantification at increasing elapsed time after mouse ear application of different inventive ICG-loaded PVP MNs (FIG. 11A and FIG. 11B).

DETAILED DESCRIPTION OF THE INVENTION

Unless defined otherwise, all technical and scientific terms used herein have the same meanings as commonly understood by one of ordinary skill in the art to which this invention belongs.

Indocyanine green (ICG): As used herein, "indocyanine green (ICG)" refers to sodium 4-[2-[(1E,3E,5E,7Z)-7-[1,1-dimethyl-3-(4-sulfonatobutyl)benzo[e]indol-2-ylidene]hepta-1,3,5-trienyl]-1,1-imethylbenzo[e]-indol-3-ium-3-yl]butane-1-sulfonate (IUPAC name; CAS Reg. No. 3599-32-4). Thus, ICG is a monosodium salt.

Poly(N-vinylpyrrolidone) (PVP): As used herein, "poly(N-vinylpyrrolidone) (PVP)" refers to a polymer made from the monomer N-vinylpyrrolidone. IUPAC name is 1-ethenylpyrrolidin-2-one and the CAS Reg. No. is 9003-39-8.

Mass ratio: As used herein, the term "mass ratio" refers to the mass of ICG as compared to mass of PVP in the compositions of the invention. For example, if the concentration of PVP in an aqueous solution is 1 g/mL and the concentration of ICG in the same aqueous solution is 0.1 mg/mL, then the mass ratio ICG:PVP is 1:10'000.

In a first aspect, the present invention provides for a solid composition comprising (a) indocyanine green (ICG), and (b) poly(N-vinylpyrrolidone) (PVP), wherein the mass ratio of said ICG to said PVP is from 1:150'000 to 1:12.5, preferably from 1:100'000 to 1:12.5, further preferably from 1:100'000 to 1:37.5, again further preferably from 1:100'000 to 1:75, again further preferably from 1:50'000 to 1:75, and wherein again further preferably said mass ratio of said ICG to said PVP is from 1:20'000 to 1:375. In a preferred embodiment, the PVP has a weight average molecular weight of below 50'000 Dalton, preferably of below 20'000 Dalton, further preferably from 500 to 20'000, again preferably from 500 to 12'000, and again further preferably from 2'000 to 11'000. PVP in this molecular weight range are known to be excreted by the kidneys.

In another aspect, the present invention provides for a solid composition comprising, preferably consisting of, (a) indocyanine green (ICG), and (b) poly(N-vinylpyrrolidone) (PVP), wherein the mass ratio of said ICG to said PVP is from 1:150'000 to 1:12.5, preferably from 1:100'000 to 1:12.5, further preferably from 1:100'000 to 1:37.5, again further preferably from 1:100'000 to 1:75, again further preferably from 1:50'000 to 1:75, and wherein again further preferably said mass ratio of said ICG to said PVP is from 1:20'000 to 1:375, and wherein further preferably said solid composition further comprises (c) optionally a buffer, and (d) optionally an osmotic agent. In a further preferred embodiment hereby, said PVP has a weight average molecular weight of below 50'000 Dalton, preferably of below 20'000 Dalton, and further preferably from 500 to 20'000. In another preferred embodiment of the present invention, said PVP has a weight average molecular weight from 500 to 12'000, preferably from 2'000 to 11'000. In a preferred embodiment, said solid composition consists of, (a) indocyanine green (ICG), and (b) poly(N-vinylpyrrolidone) (PVP), wherein the mass ratio of said ICG to said PVP is from 1:150'000 to 1:12.5, preferably from 1:100'000 to 1:12.5, further preferably from 1:100'000 to 1:37.5, again further preferably from 1:100'000 to 1:75, again further preferably from 1:50'000 to 1:75, and wherein again further preferably said mass ratio of said ICG to said PVP is from 1:20'000 to 1:375, and wherein said solid composition further comprises (c) optionally a buffer, and (d) optionally an osmotic agent. Preferably hereby, said PVP has a weight average molecular weight from 500 to 20'000, further from 500 to 12'000, preferably from 2'000 to 11'000.

In a preferred embodiment, said solid composition comprises (a) indocyanine green (ICG), and (b) poly(N-vinylpyrrolidone) (PVP), wherein the mass ratio of said ICG to said PVP is from 1:50'000 to 1:75, preferably said mass ratio of said ICG to said PVP is from 1:20'000 to 1:375. Preferably, the PVP has a weight average molecular weight of below 50'000 Dalton, preferably of below 20'000 Dalton.

In a preferred embodiment, said solid composition comprises (a) indocyanine green (ICG), and (b) poly(N-vinylpyrrolidone) (PVP), wherein the mass ratio of said ICG to said PVP is from 1:50'000 to 1:75, preferably said mass ratio of said ICG to said PVP is from 1:20'000 to 1:375. Preferably, the PVP has a weight average molecular weight of below 20'000 Dalton, preferably from 500 to 20'000, and further preferably from 2'000 to 11'000.

In a preferred embodiment, said solid composition comprises (a) indocyanine green (ICG), and (b) poly(N-vinylpyrrolidone) (PVP), wherein the mass ratio of said ICG to said PVP is from 1:20'000 to 1:375. Preferably, the PVP has a weight average molecular weight of below 20'000 Dalton, preferably from 500 to 20'000, and further preferably from 2'000 to 11'000.

The term "solid composition", as used herein, refers to the inventive composition comprising ICG and PVP in said mass ratio and which is in the solid state at NTP (Normal temperature and Pressure, i.e. 20° C. and 1 atm). Typically and preferably the solid composition has a water content of less than 5% per weight, preferably of less than 3% per weight, and further preferably of less than 1% per weight. In a further embodiment, said solid composition is essentially anhydrous. Various techniques are well-known in the art for preparing the solid compositions including, but not limited to melt-extrusion, spray-drying, lyophilization, and solution-evaporation. Preferably, the solid composition of the invention is obtained by first dissolving both components in a suitable solvent, or mixture of solvents, and then evaporating the latter. Methods used to evaporate the solvent may include placing the samples under vacuum and/or heat, spray-drying or freeze-drying, all of them are well-known processes and known to the skilled person in the art. A further method useful and typically and preferably used for the present invention to evaporate the solvent is drying the inventive compositions at room temperature and atmospheric pressure, preferably at NTP. Most conveniently the same is effected, typically and preferably, in a dry box. Solvents such as water and alcohols, and hereby methanol or ethanol, can typically be used. Preferably, the solvent is water, preferably WFI. In a further preferred embodiment of the present invention, said solid composition is a lyophilized composition obtained by freeze-drying a solution comprising ICG and PVP in a mass ratio of said ICG to said PVP from 1:150'000 to 1:12.5, preferably from 1:100'000 to 1:12.5, further preferably from 1:100'000 to 1:37.5, again further preferably from 1:100'000 to 1:75, again further preferably from 1:50'000 to 1:75, and wherein again further preferably said mass ratio of said ICG to said PVP is from 1:20'000 to 1:375. In another preferred embodiment of the present invention, solid composition is obtained by spray-drying of a solution comprising ICG and PVP in a mass ratio of said ICG to said PVP from 1:150'000 to 1:12.5, preferably from 1:100'000 to 1:12.5, further preferably from 1:100'000 to 1:37.5, again further preferably from 1:100'000 to 1:75, again further preferably from 1:50'000 to 1:75, and wherein again further preferably said mass ratio of said ICG to said PVP is from 1:20'000 to 1:375. As indicated, spray-drying and freeze-drying are well-known processes in the art and suitable spray-drying or freeze-drying parameters are also known in the art, and it is within the knowledge of a skilled artisan in the field to select appropriate parameters therefore.

In another aspect, the present invention provides for an aqueous composition obtained by dissolving the inventive solid composition in water, preferably in sterilized water, further preferably in water for injection (WFI). Preferably, the concentration of said ICG in said aqueous composition is from 0.025 mg/mL to 20 mg/mL, preferably from 0.025 mg/mL to 9.8 mg/mL, and wherein further preferably the concentration of said ICG in said aqueous composition is from 0.025 mg/mL to 5 mg/mL, again further preferably from 0.1 mg/mL to 5 mg/mL, and wherein the concentration of said PVP in said aqueous composition is from equal to or higher than 0.5 mg/mL, preferably from 0.5 mg/mL to 1.5 g/mL, and wherein further preferably the concentration of said PVP in said aqueous composition is from 7.5 mg/mL to 1.5 g/mL, again further preferably from 7.5 mg/mL to 0.5 g/mL. In another preferred embodiment, the concentration of said ICG in said aqueous composition is from 0.05 mg/mL to 20 mg/mL, preferably from 0.05 mg/mL to 9.8 mg/mL, further preferably from 0.1 mg/mL to 9.8 mg/mL, further preferably from 0.1 mg/mL to 5 mg/mL, and wherein the concentration of said PVP in said aqueous composition is from 75 mg/mL to 1.5 g/mL, preferably from 75 mg/mL to 0.5 g/mL. In a preferred embodiment, said aqueous composition shows an increase of fluorescence of said ICG of at least 10%, preferably of at least 30%, further preferably of at least 45%, as compared to a corresponding aqueous composition comprising the same concentration of ICG but lacking said PVP. In the context of the present invention, the term "an increase of fluorescence of said ICG as compared to a corresponding aqueous composition comprising the same concentration of ICG but lacking said PVP" refers, thus, to an increase which is independent of the used instruments and conditions to determine said increase. Exemplary and preferred determinations of said increase are provided in the Example section, and in particular in Example 1.

In a preferred embodiment, said aqueous composition is obtained by dissolving the inventive solid composition in WFI and the concentration of said ICG in said aqueous composition is from 0.025 mg/mL to 20 mg/mL, preferably from 0.025 mg/mL to 9.8 mg/mL, further preferably from 0.025 mg/mL to 5 mg/mL, again further preferably from 0.1 mg/mL to 5 mg/mL, and the concentration of said PVP in said aqueous composition is from 0.5 mg/mL to 1.5 g/mL, preferably from 0.5 mg/mL to 0.5 g/mL. Preferably, said aqueous composition shows an increase of fluorescence of said ICG of at least 10%, preferably of at least 30%, further preferably of at least 45%, as compared to a corresponding aqueous composition comprising the same concentration of ICG but lacking said PVP.

In another preferred embodiment, said aqueous composition is obtained by dissolving the inventive solid composition in WFI and the concentration of said ICG in said aqueous composition is from 0.1 mg/mL to 20 mg/mL, preferably from 0.025 mg/mL to 9.8 mg/mL, further preferably from 0.025 mg/mL to 5 mg/mL, again further preferably from 0.1 mg/mL to 5 mg/mL, and the concentration of said PVP in said aqueous composition is from 75 mg/mL to 1.5 g/mL, preferably from 0.5 mg/mL to 0.5 g/mL. Preferably, said aqueous composition shows an increase of fluorescence of said ICG of at least 10%, preferably of at least 30%, further preferably of at least 45%, as compared to a corresponding aqueous composition comprising the same concentration of ICG but lacking said PVP.

In another preferred embodiment, said aqueous composition is obtained by dissolving the inventive solid composition in WFI and the concentration of said ICG in said aqueous composition is from 0.1 mg/mL to 20 mg/mL, preferably from 0.025 mg/mL to 9.8 mg/mL, further preferably from 0.025 mg/mL to 5 mg/mL, again further preferably from 0.1 mg/mL to 5 mg/mL, and the concentration of said PVP in said aqueous composition is from 75 mg/mL to 1.5 g/mL, preferably from 0.5 mg/mL to 0.5 g/mL, and said aqueous composition shows an increase of fluorescence of said ICG of at least 45%, as compared to a corresponding aqueous composition comprising the same concentration of ICG but lacking said PVP.

In a further aspect, the present invention provides for an aqueous composition comprising, preferably consisting of, (a) indocyanine green (ICG) at a concentration in said aqueous composition from 0.025 mg/ml to 5 mg/ml, preferably from 0.1 mg/ml to 5 mg/ml, and (b) poly(N-vinylpyrrolidone) (PVP) at a concentration in said aqueous composition from equal to or higher than 0.5 mg/ml, and preferably at a concentration from 0.5 mg/mL to 1.5 g/mL, further preferably from 7.5 mg/mL to 1.5 g/mL, and again further preferably from 7.5 mg/mL to 0.5 g/mL and (c) optionally a buffer, and (d) optionally an osmotic agent. Preferably, water for injection (WFI) is used as the water source for the inventive aqueous composition. In another preferred embodiment, the concentration of said ICG in said aqueous composition is from 0.05 mg/mL to 5 mg/mL, preferably from 0.1 mg/mL to 5 mg/mL, and wherein the concentration of said PVP in said aqueous composition is from 75 mg/mL to 1.5 g/mL, preferably from 75 mg/mL to 0.5 g/mL. Buffers useful for the present invention include buffers from citrate, acetate, histidine and phosphate. Preferably, said aqueous composition shows an increase of fluorescence of said ICG of at least 10%, preferably of at least 30%, further preferably of at least 45%, as compared to a corresponding aqueous composition comprising the same concentration of ICG but lacking said PVP.

The composition according to the invention may, thus, be in a form of a solid, e.g. as a lyophilized preparation and composition, respectively, for reconstitution prior to use in a liquid aqueous carrier for injections. Therefore, in a further aspect, the present invention provides for a method of producing the inventive aqueous composition, wherein said method comprises reconstituting said solid composition in a physiological acceptable solution or in sterile water, preferably in water for injection (WFI). In an alternative aspect, the present invention provides for a method of producing the inventive aqueous composition, wherein said method comprises dissolving or suspending said indocyanine green (ICG) in an aqueous solution, preferably in a physiological acceptable solution or in sterile water, further preferably in water for injection (WFI), of said poly(N-vinylpyrrolidone) (PVP).

In still a further aspect, the present invention provides for a method of producing the inventive aqueous composition, wherein said method comprises dissolving or suspending the inventive solid composition in water, preferably in sterilized water, further preferably in water for injection (WFI).

In a further preferred embodiment of the present invention, the inventive compositions do not comprise an alcohol. In another embodiment, the inventive compositions of the present invention do not comprise a bovine serum albumin or a human serum albumin. In another embodiment, the inventive compositions of the present invention do not comprise any kind of a serum protein.

The inventive compositions may be packaged in any suitable manner, e.g., vials made of glass, plastic or other pharmaceutically-acceptable materials. The inventive compositions are desirably protected from exposure to light. Preferably, the inventive solid compositions are packaged in a multi-chambered vessel. Thus, in a further aspect, the present invention provides for a multi-chambered vessel which separates the inventive solid composition until it is required for diagnosis or therapy. Preferred examples of suitable multi-chambered vessels are a dual-chamber syringe and a dual chambered vial. Therefore, in another aspect, the present invention provides for a multi-chambered vessel comprising a first container and a second container, wherein said first container comprises the inventive solid composition, and wherein said second container comprises a physiological acceptable aqueous solution or sterile water, preferably water for injection (WFI). Preferably, said multi-chambered vessel is a dual-chamber syringe. Alternatively preferably, the multi-chambered vessel is a vial.

In another aspect, the present invention provides for an inventive aqueous composition or a solid composition, preferably said solid composition, for use in a method of making a microneedle device (MN device). In another very preferred aspect, the present invention provides for the use of the inventive solid composition or the inventive aqueous composition, preferably said inventive solid composition, in a method of making a microneedle device.

In again another aspect, the present invention provides a microneedle device comprising, preferably consisting of, (a) indocyanine green (ICG), and (b) poly(N-vinylpyrrolidone) (PVP), wherein the mass ratio of said ICG to said PVP is from 1:150'000 to 1:12.5, preferably from 1:100'000 to 1:12.5, further preferably from 1:100'000 to 1:37.5, again further preferably from 1:100'000 to 1:75, again further preferably from 1:50'000 to 1:75, and wherein again further preferably said mass ratio of said ICG to said PVP is from 1:20'000 to 1:375, and wherein said microneedle device further comprises (c) optionally a buffer, and (d) optionally an osmotic agent. In a further preferred embodiment, said PVP has a weight average molecular weight of below 50'000 Dalton, preferably of below 20'000 Dalton, and further preferably from 500 to 20'000. In another preferred embodiment, said PVP has a weight average molecular weight from 500 to 12'000, preferably from 2'000 to 11'000.

Microneedle devices are known to the skilled person in the art and are typically and preferably used for transport of therapeutic and biological molecules across tissue barriers such as for drug delivery. Microneedle devices and methods of making the same are, for example, described in U.S. Pat. Nos. 3,964,482; 6,334,856; 6,503,231; 6,611,707; 8,708, 966; US 2012/0265145 A1; Chu, L Y et al, Journal of Pharmaceutical Sciences, Vol. 99, 4228-4238 (2010); Park, J H et al, Journal of Controlled Release 104 (2005) 51-66; Lahiji, S F et al, Scientific Reports 5: 7914; |DOI: 10.1038/srep07914 (2015); and references cited therein.

A microneedle device typically comprises a substrate to which a plurality of microneedles are attached or integrally formed with a substrate. The substrate of the device can be constructed from a variety of materials, including metals, ceramics, semiconductors, organics, polymers, and composites. The substrate includes the base to which the microneedles are attached or integrally formed. Recently, the formation of microneedles made from biodegradable or dissolvable biocompatible polymers has been described. Thus, U.S. Pat. No. 8,708,966 described microneedles formed of a biodegradable polymer and an active agent being dispersed in said biodegradable polymer of the microneedles. The delivery of the active agent is then effected by way of biodegradation of the biodegradable polymer of the microneedles. US 2012/0265145 A1 described soluble microneedles which are mostly constituted by materials such as maltose, polylactic acid (PLA), carboxymethylcellulose (CMC), or hyaluronic acid. The material is mixed with a drug and the whole mixture forms then the microneedles. Once into the skin, microneedles degrade/dissolve, thus releasing the drug. Further dissolving polymer microneedles for controlled drug delivery and delivery using different microneedle designs have been described, by way of example, by Chu et al (Chu, L Y et al, Journal of Pharmaceutical Sciences, Vol. 99, 4228-4238 (2010) and Park, J H et al (Park J H et al, Journal of Controlled Release 104 (2005) 51-66).

Thus, in another aspect, the present invention provides for a microneedle device, preferably comprising a substrate to which a plurality of microneedles are attached or integrally formed, wherein said microneedle device is prepared with the inventive solid composition. Preferably, said solid composition comprises, preferably consists of, (a) indocyanine green (ICG), and (b) poly(N-vinylpyrrolidone) (PVP), wherein the mass ratio of said ICG to said PVP is from 1:150'000 to 1:12.5, preferably from 1:100'000 to 1:12.5, further preferably from 1:100'000 to 1:37.5, again further preferably from 1:100'000 to 1:75, again further preferably from 1:50'000 to 1:75, and wherein again further preferably said mass ratio of said ICG to said PVP is from 1:20'000 to 1:375, and wherein said microneedle device further comprises (c) optionally a buffer, and (d) optionally an osmotic agent. In a further preferred embodiment, said PVP has a weight average molecular weight of below 50'000 Dalton, preferably of below 20'000 Dalton, and further preferably from 500 to 20'000. In another preferred embodiment, said PVP has a weight average molecular weight from 500 to 12'000, preferably from 2'000 to 11'000. In a preferred embodiment, said solid composition comprises (a) indocyanine green (ICG), and (b) poly(N-vinylpyrrolidone) (PVP), wherein the mass ratio of said ICG to said PVP is from 1:50'000 to 1:75, preferably said mass ratio of said ICG to said PVP is from 1:20'000 to 1:375. Preferably, the PVP has a weight average molecular weight of below 50'000 Dalton, preferably of below 20'000 Dalton. In another preferred embodiment, said solid composition comprises (a) indocyanine green (ICG), and (b) poly(N-vinylpyrrolidone) (PVP), wherein the mass ratio of said ICG to said PVP is from 1:50'000 to 1:75, preferably said mass ratio of said ICG to said PVP is from 1:20'000 to 1:375. Preferably, the PVP has a weight average molecular weight of below 20'000 Dalton, preferably from 500 to 20'000, and further preferably from 2'000 to 11'000. In another preferred embodiment, said solid composition comprises (a) indocyanine green (ICG), and (b) poly(N-vinylpyrrolidone) (PVP), wherein the mass ratio of said ICG to said PVP is from 1:20'000 to 1:375. Preferably, the PVP has a weight average molecular weight of below 20'000 Dalton, preferably from 500 to 20'000, and further preferably from 2'000 to 11'000.

In another aspect, the present invention provides for the use of the inventive solid composition in the form of a microneedle device.

In another aspect, the present invention provides for a microneedle device, preferably comprising a substrate to which a plurality of microneedles are attached or integrally formed, wherein said microneedle device is prepared with the inventive aqueous composition.

In another aspect, the present invention provides for a microneedle device, preferably comprising a substrate to which a plurality of microneedles are attached or integrally formed, wherein said microneedles consist of the inventive solid composition. Preferably, said solid composition comprises, preferably consists of, (a) indocyanine green (ICG), and (b) poly(N-vinylpyrrolidone) (PVP), wherein the mass ratio of said ICG to said PVP is from 1:150'000 to 1:12.5, preferably from 1:100'000 to 1:12.5, further preferably from 1:100'000 to 1:37.5, again further preferably from 1:100'000 to 1:75, again further preferably from 1:50'000 to 1:75, and wherein again further preferably said mass ratio of said ICG to said PVP is from 1:20'000 to 1:375, and wherein said microneedle device further comprises (c) optionally a buffer, and (d) optionally an osmotic agent. In a further preferred embodiment, said PVP has a weight average molecular weight of below 50'000 Dalton, preferably of below 20'000 Dalton, and further preferably from 500 to 20'000. In another preferred embodiment, said PVP has a weight average molecular weight from 500 to 12'000, preferably from 2'000 to 11'000. In a preferred embodiment, said solid composition comprises (a) indocyanine green (ICG), and (b) poly(N-vinylpyrrolidone) (PVP), wherein the mass ratio of said ICG to said PVP is from 1:50'000 to 1:75, preferably said mass ratio of said ICG to said PVP is from 1:20'000 to 1:375. Preferably, the PVP has a weight average molecular weight of below 50'000 Dalton, preferably of below 20'000 Dalton. In another preferred embodiment, said solid composition comprises (a) indocyanine green (ICG), and (b) poly(N-vinylpyrrolidone) (PVP), wherein the mass ratio of said ICG to said PVP is from 1:50'000 to 1:75, preferably said mass ratio of said ICG to said PVP is from 1:20'000 to 1:375. Preferably, the PVP has a weight average molecular weight of below 20'000 Dalton, preferably from 500 to 20'000, and further preferably from 2'000 to 11'000. In another preferred embodiment, said solid composition comprises (a) indocyanine green (ICG), and (b) poly(N-vinylpyrrolidone) (PVP), wherein the mass ratio of said ICG to said PVP is from 1:20'000 to 1:375. Preferably, the PVP has a weight average molecular weight of below 20'000 Dalton, preferably from 500 to 20'000, and further preferably from 2'000 to 11'000.

In another aspect, the present invention provides for a method of making a microneedle device comprising the use of the inventive solid composition for said making of said microneedle device. Preferably, said solid composition comprises, preferably consists of, (a) indocyanine green (ICG), and (b) poly(N-vinylpyrrolidone) (PVP), wherein the mass ratio of said ICG to said PVP is from 1:150'000 to 1:12.5, preferably from 1:100'000 to 1:12.5, further preferably from 1:100'000 to 1:37.5, again further preferably from 1:100'000 to 1:75, again further preferably from 1:50'000 to 1:75, and wherein again further preferably said mass ratio of said ICG to said PVP is from 1:20'000 to 1:375, and wherein said microneedle device further comprises (c) optionally a buffer, and (d) optionally an osmotic agent. In a further preferred embodiment, said PVP has a weight average molecular weight of below 50'000 Dalton, preferably of below 20'000 Dalton, and further preferably from 500 to 20'000. In another preferred embodiment, said PVP has a weight average molecular weight from 500 to 12'000, preferably from 2'000 to 11'000. In a preferred embodiment, said solid composition comprises (a) indocyanine green (ICG), and (b) poly(N-vinylpyrrolidone) (PVP), wherein the mass ratio of said ICG to said PVP is from 1:50'000 to 1:75, preferably said mass ratio of said ICG to said PVP is from 1:20'000 to 1:375. Preferably, the PVP has a weight average molecular weight of below 50'000 Dalton, preferably of below 20'000 Dalton. In another preferred embodiment, said solid composition comprises (a) indocyanine green (ICG), and (b) poly(N-vinylpyrrolidone) (PVP), wherein the mass ratio of said ICG to said PVP is from 1:50'000 to 1:75, preferably said mass ratio of said ICG to said PVP is from 1:20'000 to 1:375. Preferably, the PVP has a weight average molecular weight of below 20'000 Dalton, preferably from 500 to 20'000, and further preferably from 2'000 to 11'000. In another preferred embodiment, said solid composition comprises (a) indocyanine green (ICG), and (b) poly(N-vinylpyrrolidone) (PVP), wherein the mass ratio of said ICG to said PVP is from 1:20'000 to 1:375. Preferably, the PVP has a weight average molecular weight of below 20'000 Dalton, preferably from 500 to 20'000, and further preferably from 2'000 to 11'000.

Thus, in this preferred aspect, the inventive compositions, preferably said solid composition, are used for making a microneedle device, and thus, the inventive compositions, preferably said solid composition, can form a device of microneedles. In another preferred aspect, the present invention provides the inventive compositions for use in a method of making a microneedle device, wherein preferably said microneedle device is used in a method of imaging the vascular system, preferably the lymphatic system, preferably in a method of real-time quantitative imaging of the lymphatic system. In a preferred embodiment hereby, said imaging is by near-infrared (NIR) imaging. In another preferred embodiment of the present invention, said microneedle device is used in a method of imaging the vascular system and in particular the lymphatic system, wherein said imaging of said lymphatic system is for mapping the sentinel lymph node or nodes of a tumor in a mammal, preferably in a human.

In a preferred embodiment, said the microneedle device comprises a substrate to which a plurality of microneedles are attached or integrally formed. Preferably, ICG is solely comprised by the microneedles (MNs) and the substrate does not comprise said ICG. In an alternative embodiment, the said MNs and said substrate of said MN device comprises ICG.

The use of the MNs-device made in accordance with the present invention leads to the administration of ICG as the imaging agent in a pain-free, carefully depth-localized manner. Moreover, the administration does not require particular skills or specialized personnel and could therefore be done by the patients themselves or by un-specialized caregivers. Furthermore, the use of the MNs-device made in accordance with the present invention does not require any pre-treatment before administration, and is thus "ready to use", and can be done without generating sharp/dangerous waste which needs specialized disposal.

The MNs can have different shapes. Typically and preferably, said plurality of microneedles has tapered or flat walls; square, circular or any other bi-dimensional basis perimeter with lengths/width less than 1 mm. The device can be produced to have any number n of MNs on the backing layer which n is equal and/or higher than 1. The backing layer can have any tridimensional shape and sizes in order to best adapt to the application surface. The MNs can be produced using different ICG:PVP mass ratios from 1:150'000 to 1:12.5, preferably from 1:100'000 to 1:12.5, further preferably from 1:100'000 to 1:37.5, again further preferably from 1:100'000 to 1:75, again further preferably from 1:50'000 to 1:75, and again further preferably from 1:20'000 to 1:375. The device can be applied to the skin for different elapsed times typically and preferably higher than 1 second, further preferably between 1 second to 5 minutes. In a preferred embodiment, said MNs have a tapered pyramidal shape with typically and preferably a square base of 150 m×150 µm; a length of 400 µm; and a peak-to-peak distance of 500 µm. Preferably, the MN device is applied using a spring-loaded applicator.

Importantly, the prepared MNs of the present invention typically and preferably have the mechanical features allowing the penetration of the epidermal layer and the physical-chemical properties allowing the visualization of the imaging agent underneath the epidermal layer.

In another aspect, the present invention provides for a solid composition or an aqueous composition for use in the preparation of a formulation for the imaging of the vascular system, preferably for imaging of the lymphatic system. In a further aspect, the present invention provides for a solid composition or an aqueous composition for use in the preparation of a formulation for obtaining an angiographic image of a tissue. Preferably, said tissue is the eye, lung, gastrointestinal tract, bladder, pancreas, gall bladder, sinus, trachea, liver, kidney, heart, cervix, brain, ovary, prostate, stomach or skin, and wherein preferably said tissue is the eye, heart, liver and stomach. In still another aspect, the present invention provides for a solid composition or an aqueous composition for use in the preparation of a formulation for the imaging of the perfusion of a tissue. Preferably, said tissue is the eye, lung, gastrointestinal tract, bladder, pancreas, gall bladder, sinus, trachea, liver, kidney, heart, cervix, brain, ovary, prostate, stomach or skin, and wherein preferably said tissue is the eye, heart, liver and stomach.

In another aspect, the present invention provides a formulation comprising the inventive solid composition or the inventive aqueous composition. Thus, in another aspect, the present invention provides for a formulation comprising, preferably consisting of, (a) indocyanine green (ICG), and (b) poly(N-vinylpyrrolidone) (PVP), wherein the mass ratio of said ICG to said PVP is from 1:150'000 to 1:12.5, preferably from 1:100'000 to 1:12.5, further preferably from 1:100'000 to 1:37.5, again further preferably from 1:100'000 to 1:75, again further preferably from 1:50'000 to 1:75, and wherein again further preferably said mass ratio of said ICG to said PVP is from 1:20'000 to 1:375, and wherein further preferably said formulation further comprises (c) optionally a buffer, and (d) optionally an osmotic agent. In a further preferred embodiment hereby, said PVP has a weight average molecular weight of below 50'000 Dalton, preferably of below 20'000 Dalton, and further preferably from 500 to 20'000. In another preferred embodiment, said PVP has a weight average molecular weight from 500 to 12'000, preferably from 2'000 to 11'000.

In still another aspect, the present invention provides for the use of a solid composition or of an aqueous composition in a method of preparation of a formulation for the imaging of the vascular system, preferably for imaging of the lymphatic system. In further aspect, the present invention provides for the use of a solid composition or of an aqueous composition in a method of preparation of a formulation for obtaining an angiographic image of a tissue. Preferably, said tissue is the eye, lung, gastrointestinal tract, bladder, pancreas, gall bladder, sinus, trachea, liver, kidney, heart, cervix, brain, ovary, prostate, stomach or skin, and wherein preferably said tissue is the eye, heart, liver and stomach. In still another aspect, the present invention provides for the use of a solid composition or of an aqueous composition in a method of preparation of a formulation for the imaging of the perfusion of a tissue. Preferably, said tissue is the eye, lung, gastrointestinal tract, bladder, pancreas, gall bladder, sinus, trachea, liver, kidney, heart, cervix, brain, ovary, prostate, stomach or skin, and wherein preferably said tissue is the eye, heart, liver and stomach.

In another aspect, the present invention provides for a solid composition or an aqueous composition for use in diagnosis, preferably for use in diagnosis of a disease or malfunction of a mammal, preferably of a human. As indicated, the inventive compositions allow for a precise quantitative evaluation of lymphatic function and structure due to the higher initial fluorescence and the absence of de-quenching phase after in vivo administration.

As indicated, the FDA has approved ICG as an injectable contrast agent for use in determining hepatic function, cardiac output and liver blood flow as well as for ophthalmic angiography. Moreover, ICG use allows non-invasive monitoring of liver or splanchnic perfusion (by monitoring the changes in the ICG plasma disappearance rate, this method is suitable as a parameter for predicting the probability of survival of intensive-care surgical patients).

Thus, in a further preferred aspect, the present invention provides for a solid composition or an aqueous composition for use in a method of imaging of the vascular system, preferably for imaging of the lymphatic system. Moreover, in another preferred aspect, the present invention provides for a solid composition or an aqueous composition for use in a method of obtaining an angiographic image of a tissue. Furthermore, in again another preferred aspect, the present invention provides for a solid composition or an aqueous composition for use in a method of the perfusion of a tissue. Preferably, the tissue is the eye, lung, gastrointestinal tract, bladder, pancreas, gall bladder, sinus, trachea, liver, kidney, heart, cervix, brain, ovary, prostate, stomach or skin, and wherein preferably said tissue is the eye, heart, liver and stomach. In a further preferred embodiment, the present invention provides for a solid composition or an aqueous composition for use in a method of real-time quantitative imaging the lymphatic system. In a preferred embodiment, said imaging is by near-infrared (NIR) imaging. Typically and preferably, said method comprises the intradermal, subcutaneous, intravenous, intravitreal or intramuscular administration of the inventive composition to a mammal, preferably to a human, preferably by way of intradermal administration of said inventive composition in a human, where it is taken up by the lymphatic vessels of said human. In a preferred embodiment, said method further comprises applying near infrared (NIR) wavelengths, typically and preferably by a laser diode or a LED, and further imaging said lymphatic system of said human using an image providing device such as a charge-coupled device (CCD) or electron multiplying (EM)-CCD camera with appropriate optics and filters. In another preferred embodiment of the present invention, said imaging of said lymphatic system is for mapping the sentinel lymph node or nodes of a tumor in a mammal, preferably in a human. In another embodiment, said imaging of the lymphatic system is for quantifying lymphatic pumping capacity in vivo, assessing lymphedema, skin cancer, sentinel lymph node mapping after breast cancer surgery and the like.

Further aspects of the present invention include the use of the inventive solid composition or the inventive aqueous composition in a method of imaging the vascular system, preferably of imaging the lymphatic system, further preferably in a method of real-time quantitative imaging the lymphatic system.

In another aspect, the present invention provides for the use of the inventive solid composition or the inventive aqueous composition or the inventive microneedle device, in a method of obtaining an angiographic image of a tissue or in a method of imaging the perfusion of a tissue, preferably in a method of obtaining an angiographic image of a tissue. Preferably, the tissue is the eye, lung, gastrointestinal tract, bladder, pancreas, gall bladder, sinus, trachea, liver, kidney, heart, cervix, brain, ovary, prostate, stomach or skin, and wherein further preferably said tissue is the eye, heart, liver and stomach. In a preferred embodiment, said imaging is by near-infrared (NIR) imaging. Typically and preferably, said method comprises the intradermal, subcutaneous, intravenous, intravitreal or intramuscular administration of the inventive composition to a mammal, preferably to a human, preferably by way of intradermal administration of said inventive composition in a human, where it is taken up by the lymphatic vessels of said human. In a preferred embodiment, said method further comprises applying near infrared (NIR) wavelengths, typically and preferably by a laser diode, and further imaging said lymphatic system of said human using an image providing device such as a charge-coupled device (CCD) or electron multiplying (EM)-CCD camera with appropriate optics and filters. In another preferred embodiment of the present invention, said imaging of said lymphatic system is for mapping the sentinel lymph node or nodes of a tumor in a mammal, preferably in a human. In another embodiment, said imaging of the lymphatic system is for quantifying lymphatic pumping capacity in vivo, assessing lymphedema, skin cancer, sentinel lymph node mapping after breast cancer surgery and the like.

Moreover, further aspects of the present invention include the inventive compositions for use in therapy of a mammal, preferably of a human, preferably for use in therapy of a disease or malfunction of a mammal, preferably of a human. More preferably, said therapy is a photodynamic therapy (PDT), preferably a PDT for skin tumors. PDT and its applications are known to the skilled person in the art and are described, for example, in US 2005/0265594 and by Isakau et al (Isakau, H A et al.; Journal of Photochemistry and Photobiology B: Biology 92 (2008) 165-174). Moreover, the present invention provides for said inventive compositions or said solid compositions for use in a therapy for capillary malformations (CM), wherein said inventive compositions or said solid compositions are used in combination with a diode laser therapy. The use of ICG has already been suggested for diode laser therapy of CM (Klein, A et al, Lasers in Surgery and Medicine 45:216-224 (2013)). Said therapeutic methods comprise administration of the inventive composition to said human and applying radiation of a type and in an amount effective to provide photodynamic therapy to said human, preferably to provide photodynamic therapy to skin tumor of said human. Since the inventive compositions provide an increase in ICG fluorescence as well as ICG absorbance in the presence of PVP the efficacy of the photo-thermal activity is increased while the required dosage can be decreased.

Furthermore, the present invention provides for inventive compositions and inventive multi-chambered vessels for use in a diagnostic or therapeutic method of a disease or malfunction of a mammal, preferably of a human, wherein said disease is a neoplastic disease, wherein preferably said neoplastic disease is from lung cancer, endobronchial lung cancer, urinary bladder cancer, esophagus cancer, skin cancer, breast cancer, brain tumor, colorectal cancer, gastric cancer, or gynecologic malignancies, more preferably skin cancer.

Moreover, the present invention provides for inventive compositions and inventive multi-chambered vessels for use in a diagnostic or therapeutic method of a disease or malfunction of a mammal, preferably of a human, wherein said disease is a skin disease, and wherein preferably said skin disease is psoriasis, or UV radiation-induced skin keratosis.

In addition, the present invention provides for inventive compositions and inventive multi-chambered vessels for use in a diagnostic or therapeutic method of a disease or malfunction of a mammal, preferably of a human, wherein said disease is an ophthalmic disease, wherein preferably said ophthalmic disease is age-related macular degeneration or the exudative form of age-related macular degeneration.

Furthermore, several new surgical applications relying on near infrared fluorescence angiography are suitable for the inventive compositions including plastic surgery—skin and muscle transplants, and determination of amputation level; abdominal surgery—gastrointestinal anastomosis; general surgery—wound healing and ulcers; internal medicine—diabetic extremities; heart surgery—aortocoronary bypasses; neurology—a tracer in cerebral perfusion diagnostics; and with stroke patients—monitoring.

Typically and preferably, the methods comprise the intradermal, subcutaneous, intravenous, intravitreal or intramuscular administration of the inventive composition to a mammal, preferably to a human, preferably by way of intradermal administration of said inventive composition in a human.

EXAMPLES

Example 1

Preparation of Inventive PVP-ICG Formulations and their In Vitro Fluorescence Quantification This experiment was performed using Kollidon® 12 PF purchased from BASF. Kollidon® 12 PF is poly(N-vinylpyrrolidone) (PVP) having a weight average molecular weight ($M_w$) from 2'000-3'000 as determined by light scattering methods known to the skilled person in the art.

0.25 mL of PVP-water (Kollidon® 12 PF, BASF) and 0.25 mL of freshly prepared ICG-water (IR-125, Acros Organics) were mixed to have the desired final concentrations (PVP: 0, 0.25, 0.75, 1.5, 2.5, 7.5, 15, 25, 75, 150, 250 mg/mL; ICG: 0.2 mg/mL equivalent to ICG:PVP mass ratios: 1:0, 1:1.25, 1:3.75, 1:7.5, 1:12.5, 1:37.5, 1:75, 1:125, 1:375, 1:750, 1:1250). The solutions were vigorously mixed by vortexing.

The fluorescence signal was then measured with a microplate reader (Infinite 200 Pro, TECAN Ltd., Männerdorf, Switzerland) using a quartz 96-wells plate. λex/em=700/824 nm.

Table 1 lists the obtained results by way of the normalized fluorescence signal of ICG compared to ICG-water, and thus by way of the N-fold fluorescence signal increase, in relation to the mass ratio of ICG:PVP within the investigated aqueous solution.

TABLE 1

| Mass Ratio ICG:PVP | 1:0 | 1:1.25 | 1:3.75 | 1:7.5 | 1:12.5 | 1:37.5 | 1:75 | 1:125 | 1:375 | 1:750 | 1:1250 |
|---|---|---|---|---|---|---|---|---|---|---|---|
| N-fold fluorescence | 1.00 | 0.98 | 0.92 | 1.00 | 1.09 | 1.48 | 2.17 | 3.08 | 8.79 | 12.87 | 13.76 |

Figure 1A:
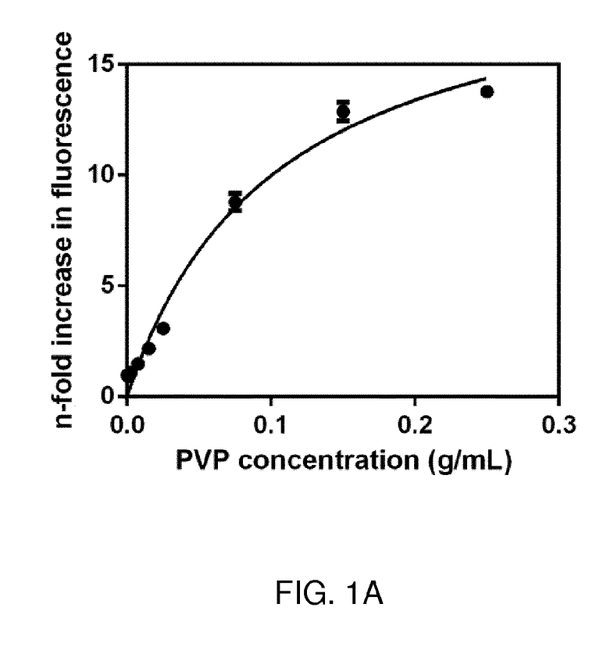
FIG. 1A: N-fold fluorescence signal increase (compared to ICG-water) of ICG in the presence of increasing concentrations of Kollidon® 12 PF.

FIG. 1A further illustrates the obtained results and shows, as well, the ability of PVP to increase ICG fluorescence in a concentration dependent fashion. In further detail, not only did the ICG fluorescence significantly increase already at a mass ratio of ICG:PVP of 1:12.5, but it showed an even further very strong increase when the mass ratio was further increased.

Figure 1B:
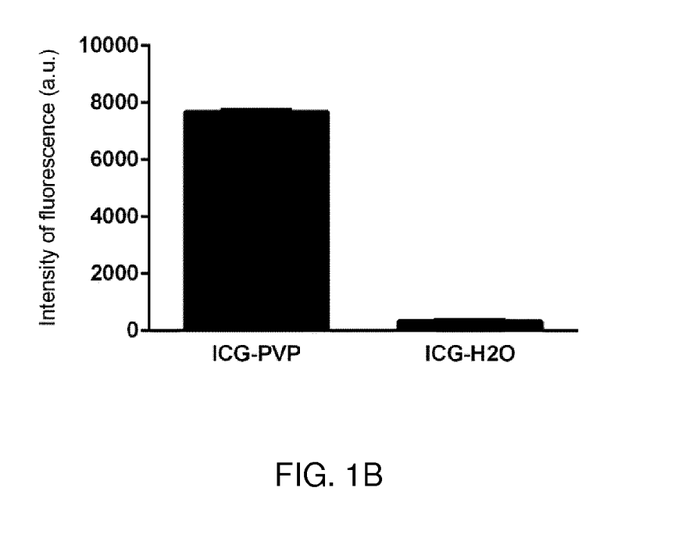
FIG. 1B: Fluorescence signal of aqueous ICG with a concentration of 9.8 mg/mL alone and in the presence of Kollidon®12 PF.

Analogously, an inventive PVP-ICG formulation was prepared with the final concentrations of ICG of 9.8 mg/mL and of PVP-water (Kollidon® 12 PF) of 0.25 g/mL (mass ratio ICG:PVP of 1:25.5). In the manner indicated above, the fluorescence signal was then measured. FIG. 1B shows that PVP increases the fluorescence of ICG at this concentration and ratio as well.

Example 2

Preparation of Inventive PVP-ICG Formulations and their In Vitro Fluorescence Quantification This experiment was performed using Kollidon® 17 PF purchased from BASF. Kollidon® 17 PF is poly(N-vinylpyrrolidone). Kollidon® 17 PF is poly(N-vinylpyrrolidone) (PVP) having a weight average molecular weight ($M_w$) from 7'000-11'000 as determined by light scattering methods known to the skilled person in the art.

0.25 mL of PVP-water (Kollidon® 17 PF, BASF) at 0.5 g/mL or distilled water were added to 0.25 mL of freshly prepared water solutions of ICG (0.05, 0.12 and 0.3 mg/mL, IR-125, Acros Organics, Geel, Belgium) to obtain the following final concentrations: PVP: 0.25 g/mL; ICG: 0.025, 0.06 and 0.15 mg/mL, equivalent to mass ratios: 1:10'000, 1:4'166 and 1:1'666. The solutions were then vigorously mixed by vortexing.

The fluorescence signal was then measured with a microplate reader (Infinite 200 Pro, TECAN Ltd., Männerdorf, Switzerland) using a quartz 96-well plate. $\lambda_{Ex/Em}$: 770/818 nm.

Figure 2:
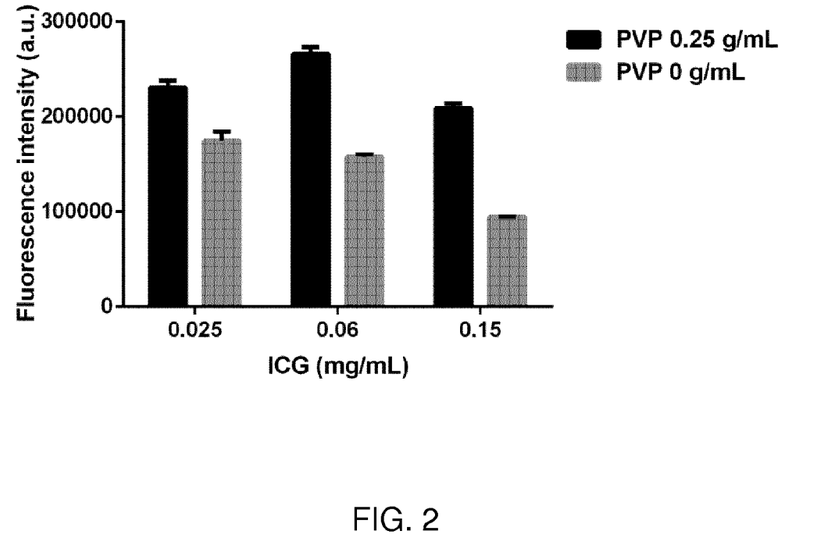
FIG. 2: Fluorescence signal of different ICG concentrations in water and in the presence of Kollidon®17 PF.

FIG. 2 shows the ability of PVP to significantly increase ICG fluorescence. Thus, the intensity of ICG fluorescence is significantly increased in presence of PVP compared to water solutions (ICG at 0.025 mg/mL n-fold increase of 1.32, ICG at 0.06 mg/mL n-fold increase of 1.68, ICG at 0.15 mg/mL n-fold increase of 2.2).

Example 3

Figure 3:
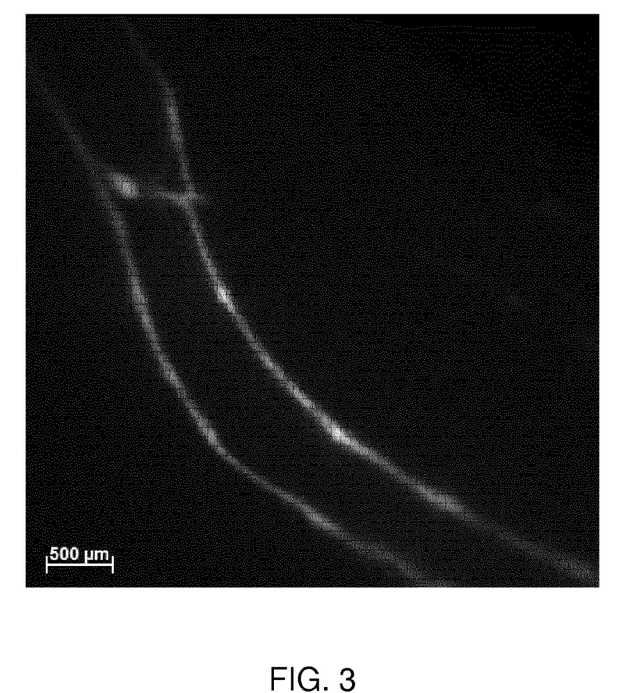
FIG. 3: Fluorescence stereomicroscope visualization of skin afferent collecting lymphatic vessel architecture after injection of Kollidon®12 PF-ICG.

Real Time Afferent Lymphatics Vessels Visualization of Inventive PVP-ICG Formulations 3 mL of PVP-water (Kollidon® 12 PF, BASF, 0.4 g/mL) or distilled water were added to 0.25 mg of dry ICG (IR-125, Acros Organics), the former corresponding to a mass ratio of ICG to PVP of 1:4800, and vigorously mixed by vortexing. 5 µL of the obtained solution were then intradermally injected into the paw of anesthetized (intraperitoneal injection of 0.2 mg/kg medetomidine and 80 mg/kg ketamine) Prox1-GFP transgenic mice using a 29 G standard needle. Immediately after injection, the animals were placed under fluorescence stereomicroscope and the lower-limb collecting lymphatic vessels architecture was imaged ($\lambda_{Ex/Em}$: 770/832 nm, FIG. 3).

Example 4

Real Time Clearance Evaluation of Inventive PVP-ICG Formulations 3 mL of PVP-water (Kollidon® 12 PF, BASF, 0.4 g/mL) or distilled water were added to 0.25 mg of dry ICG (IR-125, Acros Organics), the former corresponding to a mass ratio of ICG to PVP of 1:4800, and vigorously mixed by vortexing. 3 µL of the obtained solution were then intradermally injected into the ears of isoflurane anesthetized Prox1-GFP transgenic mice using a 29 G standard needle. Immediately after injection, the animals were placed within the IVIS system and observed (t=0 images). The animals were then subsequently observed after increasing elapsed times (1, 2, 4, 6 and 24 h). During each observation, the animals were anesthetized with isoflurane but were allowed to recover and move freely between time points. All IVIS parameters were kept constant throughout the whole experiment ($\lambda_{Ex/Em}$: 745/800 nm; exposure time: 4 s; binning: 2). Regions of interest (ROIs) were carefully drawn on t=0 in vivo images and kept constant for all the time points. The intensity of fluorescence was automatically obtained using the IVIS Living Image software (Caliper Life Sciences) for each image. Mean±SD (n=3). (FIG. 4 and FIG. 5)

Once injected intradermally, the fluorescent signal at the site of injection can be quantitatively visualized after increasing elapsed times, leading to determination of the clearance kinetics (half-lives, rate constants) which correlate with lymphatic functionality.

Figure 4:
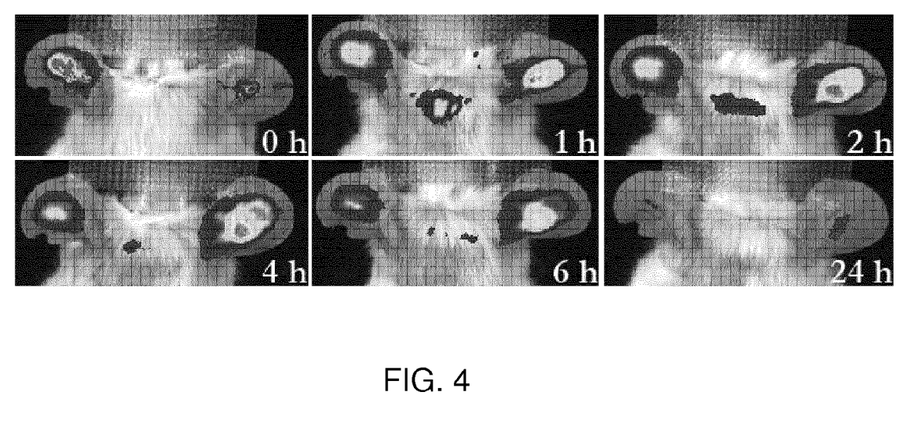
FIG. 4: Representative sequential fluorescent observations of mouse ear injection of an inventive PVP-ICG composition (left ear) and water-ICG (right ear) with IVIS Spectrum imaging system.
Figure 5:
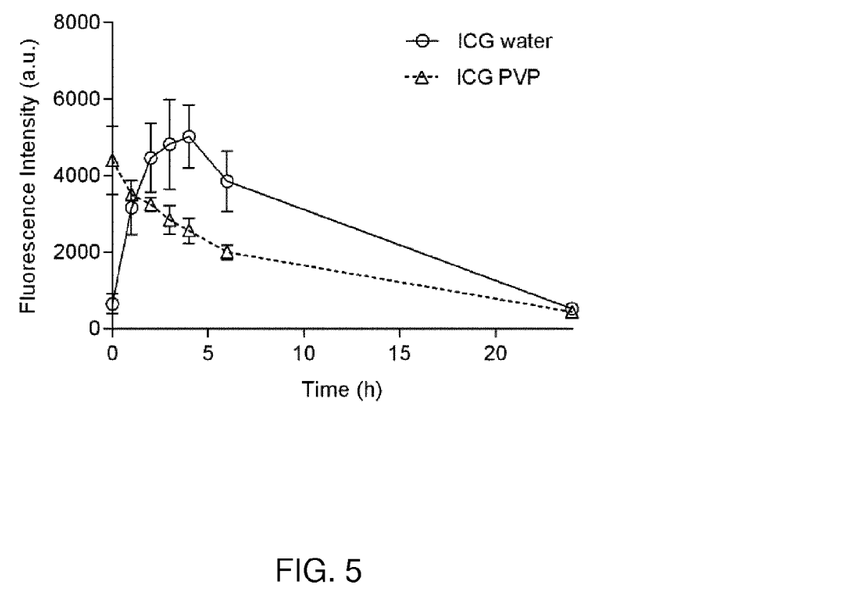
FIG. 5: Fluorescence signal quantification at increasing elapsed time after mouse ear injection of water-ICG and an inventive PVP-ICG composition.

FIG. 4 shows the images of one representative animal. Water-ICG solution was injected into the right ear and PVP-ICG aqueous solution was injected into the left ear. The fluorescent signal was followed as a function of time (0, 1, 2, 4, 6, and 24 h). FIG. 5 shows the fluorescence intensities quantification of the ear ROIs as a function of time. Importantly, the fluorescent signal after administration of the inventive ICG-PVP solution does not show a fluorescence de-quenching phase, i.e. an increase of signal over early time points as in the case of ICG-water injection.

Example 5

Preparation of Microneedles from Inventive PVP-ICG Formulations

The MNs-device is prepared by the mold-casting method, adapting a protocol previously described using MNs female molds (Micropoint Technologies, Singapore) with the desired number and shape of microneedles. Approximately 100 µL of the Kollidon® 12 PF solution in deionized water (0.9375 g/mL) containing ICG (0.0825 mg/mL) (ICG:PVP mass ratio 1:11'363) was casted on the mold and centrifuged at 2300×g, 15° C. for 5 min. The filling/centrifugation step was repeated three times, and every time the mold was turned by 180° in the plane perpendicular to the plate. After the last centrifugation, the mold was cleaned to remove the exceeding solution. Then, the mold was placed for 30 min under a reduced pressure desiccator (60 mbar). Approximately 100-200 µL of PVP in deionized water without dye were casted on the mold and centrifuged. Finally, 100-200 µL of PVP in deionized water were added on the mold and let dry at room temperature for at least 1 day. The obtained device was then carefully removed from the mold and stored in dry atmosphere.

Figure 6:
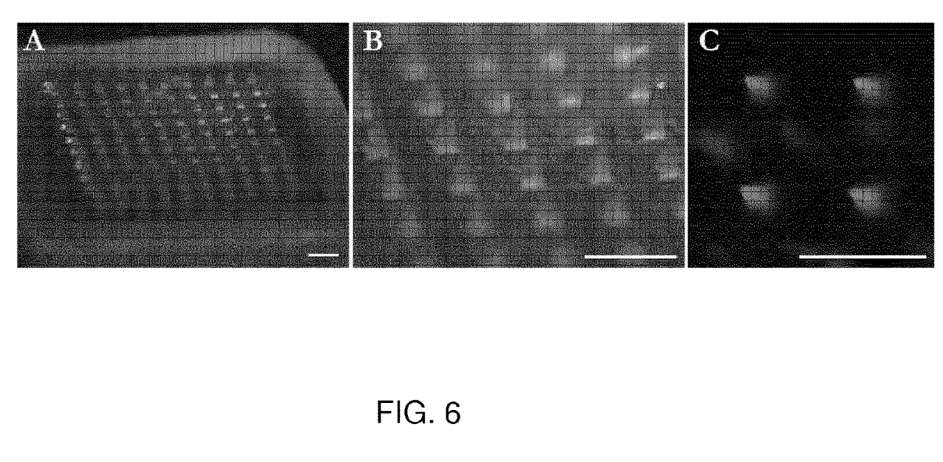
FIG. 6: Stereomicroscope images of (A) whole PVP (Kollidon®12 PF, BASF) MNs device containing ICG within the MNs, (B) zoom on few MNs and (C) fluorescence stereomicroscope observation ($\lambda_{Ex/Em}$: 770/832 nm; exposure time: 20 ms). Scale bar: 500 μm

In Vitro Observation: The obtained MNs-device was observed under a bright field stereomicroscope showing the presence of the array of pyramidal-shaped MNs (FIG. 6A-B). Fluorescence stereomicroscope observations demonstrate the presence of fluorescence (ICG) within the MNs matrix (FIG. 6C). ($\lambda_{Ex/Em}$: 770/832-7 nm)

Example 6

Preparation of Microneedles from Inventive PVP-ICG Formulations

PVP Microneedles-Based Formulation: the PVP-ICG formulation-based MNs device was produced following the protocol described in Example 5 but starting from a Kollidon® 12 PF aqueous solution (0.9375 g/mL) containing ICG (0.825 mg/mL). ICG:PVP mass ratio 1:1'136.

Figure 7:
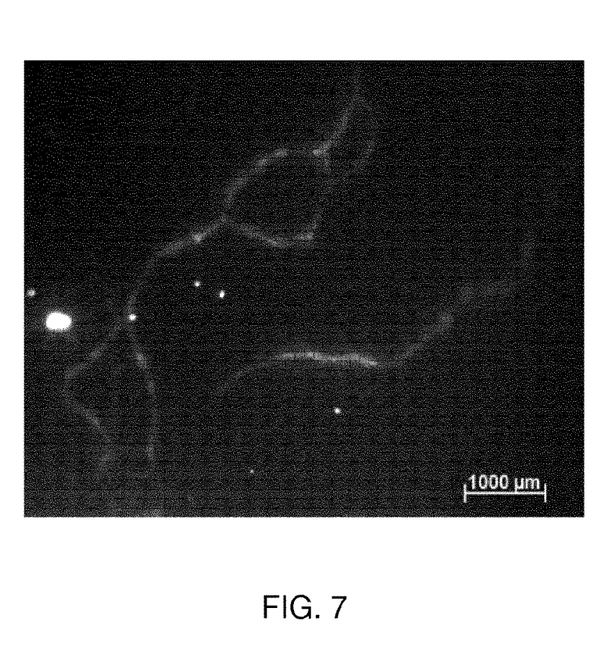
FIG. 7: Fluorescence stereomicroscope visualization of skin afferent lymphatic vessel architecture after MNs application.

Real Time Afferent Lymphatic Vessels Visualization: ICG loaded MNs-devices were applied on the lower back of anesthetized (intraperitoneal injection of 0.2 mg/kg medetomidine and 80 mg/kg ketamine) C57BL/6 albino mice using a commercially available spring-loaded applicator (Micropoint Technologies, Singapore). After spring release, the applicator and associated MNs-device were kept in position for 3 minutes. Immediately after, the surface of the injection site was carefully cleaned and the region surrounding the application visualized with a fluorescence stereomicroscope ($\lambda_{Ex/Em}$: 770/832 nm). FIG. 7 shows the visualization of the architecture of collecting lymphatic vessels spreading from the application area.

Example 7

Preparation of Microneedles from Hyaluronic Acid (HA)-Based Formulations

Approximately 100 µL of a hyaluronic acid (HA) (high molecular weight) solution in deionized water (15 mg/mL) containing ICG (0.0825 mg/mL) (HA-ICG) was casted on the mold and centrifuged at 2300×g, 15° C. for 5 min. The filling/centrifugation step was repeated three times, and every time the mold was turned by 180° in the plane perpendicular to the plate. After the last centrifugation, the mold was cleaned to remove the exceeding solution. Then, the mold was placed for 30 min under a reduced pressure desiccator (60 mbar). Approximately 100-200 L of HA in deionized water without dye were casted on the mold and centrifuged. Finally, 100-200 µL of HA in deionized water were added on the mold and let dry at room temperature for at least 1 day. The obtained device was then carefully removed from the mold and stored in dry atmosphere.

Figure 8:
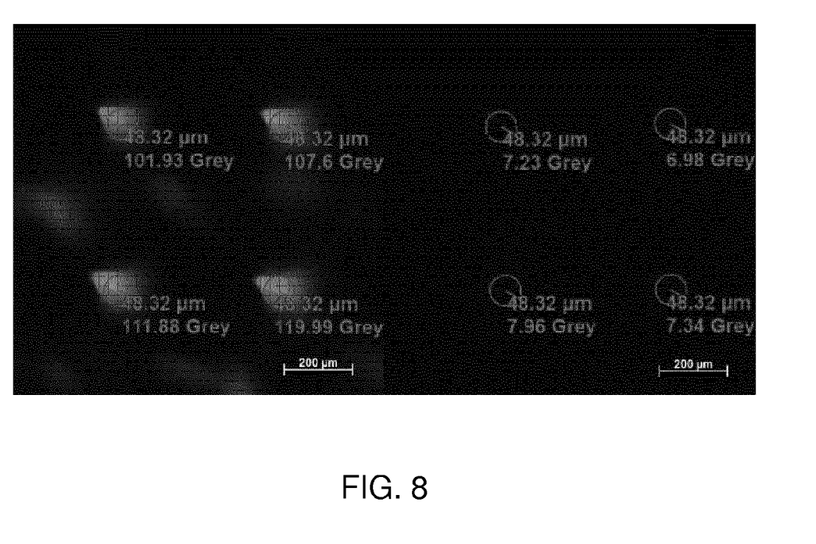
FIG. 8: Fluorescent stereomicroscope observation of MNs made of PVP (left) or HA (right) both containing the same amount of ICG.

In Vitro Fluorescence Observation: FIG. 8 shows fluorescence stereomicroscope images of MNs made of PVP or hyaluronic acid (high molecular weight) containing the same amount of ICG (0.25 10E-3 mg); corresponding to ICG:PVP mass ratio of 1:11'363 and ICG:HA mass ratio of 1:1'818. Although some fluorescence is detected also in MNs made of HA, the ICG fluorescence is drastically higher in the PVP-based formulation.

Example 8

Preparation of Microneedles from Inventive PVP-ICG Formulations

PVP Microneedles-Based Formulation: the PVP-ICG formulation-based MNs device was produced following the protocol described in Example 5 but starting from a Kollidon® 12 PF aqueous solution (0.9375 g/mL) containing ICG (0.825 mg/mL). ICG:PVP mass ratio 1:1'136.

Figure 9:
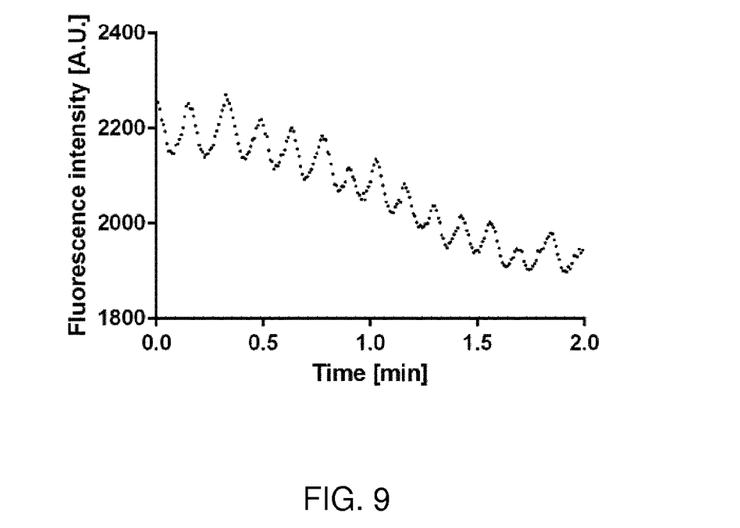
FIG. 9: Collecting lymphatic vessels contractility waves.

Collecting Lymphatic Vessel Pumping Visualization: ICG loaded MNs-devices were applied on the ear of anesthetized (intraperitoneal injection of 0.2 mg/kg medetomidine and 80 mg/kg ketamine) Prox1-GFP mice using a commercially available spring-loaded applicator (Micropoint Technologies, Singapore). After spring release, the applicator and associated MNs-device were kept in position for 3 minutes. Immediately after, the surface of the injection site was carefully cleaned and region surrounding the application visualized with a fluorescence stereomicroscope to identify the collecting lymphatic vessels. A ROI was drawn on a visualized vessel and the fluorescence intensity was measured as function of time (500 ms time frame, for 5 minutes) (FIG. 9), enabling the pumping frequency quantification (±7 contractions/minute).

Example 9

Preparation of Microneedles from Inventive PVP-ICG Formulations

PVP Microneedles-Based Formulation: the PVP-ICG formulation-based MNs device were produced as described in Example 5 and
A) starting from a Kollidon® 12 PF aqueous solution (0.9375 g/mL) containing ICG (0.0825 mg/mL). ICG:PVP mass ratio 1:11'363;
B) starting from a Kollidon® 12 PF aqueous solution (0.9375 g/mL) containing ICG (0.0082 mg/mL). ICG:PVP mass ratio 1:113'636

Figure 10:
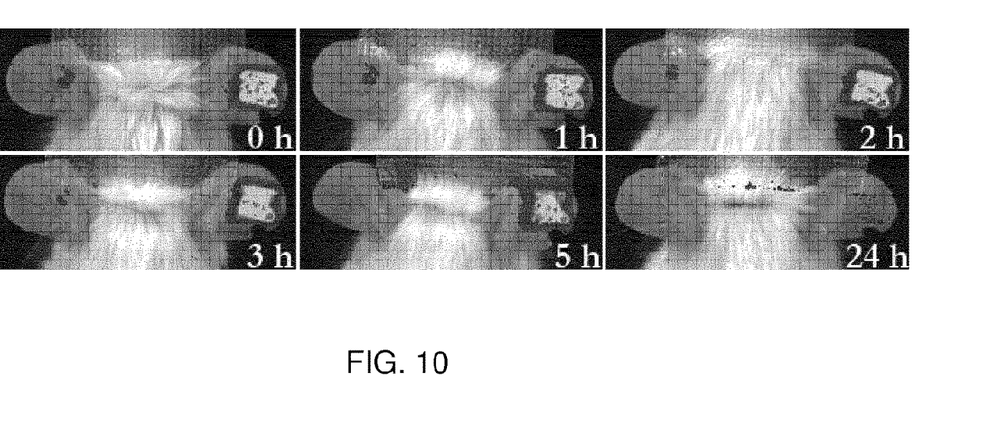
FIG. 10. Representative sequential fluorescent observations of mouse ear (right ear) after application of ICG-loaded PVP MNs with the IVIS Spectrum imaging system.
Figure 11A:
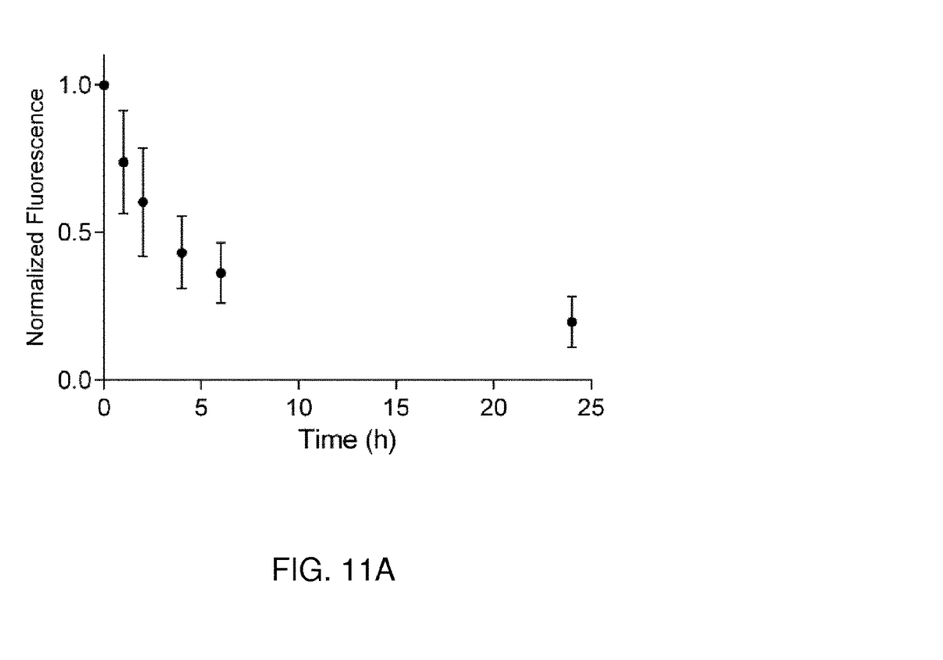
Figure 11B:
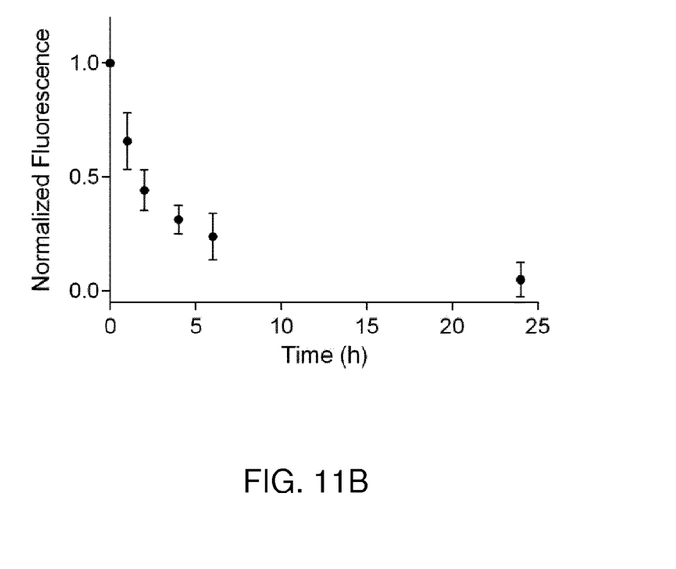

Real Time Clearance Imaging: ICG loaded MNs-devices were applied on the ear of isoflurane-anesthetized C57BL/6 albino mice using a commercially available spring-loaded applicator (Micropoint Technologies, Singapore). After spring release, the applicator and associated MNs-device were kept in position for 5 minutes. Immediately after, the surface of the ear was carefully cleaned and the animals were placed within the IVIS system and observed (t=0 images). The animals were then subsequently observed after increasing elapsed times (1, 2, 4, 6 and 24 h). During each observation, the animals were anesthetized with isoflurane but were allowed to recover and move freely between time points. All IVIS parameters were kept constant throughout the whole experiment ($\lambda$Ex/Em: 745/800 nm; exposure time: 4 s; binning: 4). Regions of interest (ROIs) were carefully drawn on t=0 in vivo images and kept constant for all time points. FIG. 10 shows the images of one representative animal with application to the right ear of composition A). The intensity of fluorescence was automatically obtained using the IVIS Living Image software (Caliper Life Sciences) for each image. The values were then normalized to t=0 image and plotted vs time (FIG. 11A for A) and FIG. 11B for B)).

Example 10

Preparation of Microneedles from Inventive PVP-ICG Formulations

PVP Microneedles-Based Formulation: the PVP-ICG formulation-based MNs device was produced following the protocol described in Example 5 but starting from a Kollidon® 12 PF aqueous solution (0.9375 g/mL) containing ICG (0.825 mg/mL). ICG:PVP mass ratio 1:1'136.

Figure 12:
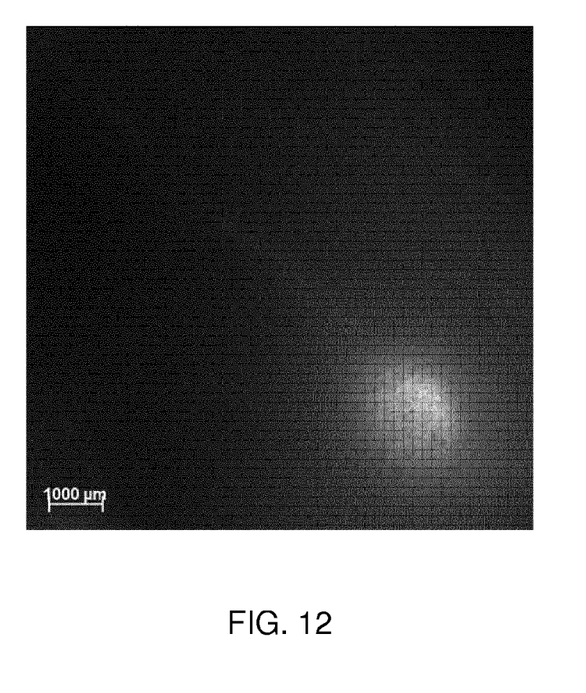
FIG. 12. Fluorescent stereomicroscope visualization of draining lymph node and inguinal node-to-axillary node efferent collecting lymphatic vessel.

Draining Lymph Node Identification and Imaging: ICG loaded MNs-devices were applied on the lower back of anesthetized (intraperitoneal injection of 0.2 mg/kg medetomidine and 80 mg/kg ketamine) C57BL/6 albino mice using a commercially available spring loaded applicator (Micropoint Technologies, Singapore). After spring release, the applicator and associated MNs-device were kept in position for 3 minutes. By following the fluorescent signal coming from the afferent vessels, the proximal draining lymph node (here the inguinal) was localized and visualized (FIG. 12). The efferent lymphatic vessel, exiting the lymph node was also identified.

The invention claimed is:
1. A microneedle device comprising a substrate to which a plurality of microneedles are attached or integrally formed, wherein said microneedles consist of a solid composition comprising (a) indocyanine green (ICG), and (b) poly(N-vinylpyrrolidone) (PVP), wherein the weight average molecular weight of PVP is 2,000 to 11,000 Dalton, and wherein the mass ratio of said ICG to said PVP is from 1:150,000 to 1:125.
2. The microneedle device of claim 1, wherein said microneedle device comprises a substrate to which a plurality of microneedles are attached or integrally formed.
3. The microneedle device of claim 1, wherein the mass ratio of ICG to PVP of the solid composition is from 1:100,000 to 1:125.
4. The microneedle device of claim 1, wherein the mass ratio of ICG to PVP of the solid composition is 1:125, 1:375, 1:750, or 1:1250.
5. The microneedle device of claim 1, wherein the mass ratio of ICG to PVP of the solid composition is from 1:50,000 to 1:125.
6. The microneedle device of claim 1, wherein the mass ratio of ICG to PVP of the solid composition is from 1:20,000 to 1:375.
7. The microneedle device of claim 1, wherein the PVP has a weight average molecular weight of 7,000 to 11,000 Dalton.

* * * * *